(12) United States Patent
Tsiper (10) Patent No.: US 8,377,484 B1
(45) Date of Patent: Feb. 19, 2013

(54) TUMOR ENCAPSULATION FOR PREVENTION AND TREATMENT OF METASTATIC CANCER DISEASE

(75) Inventor: Maria V. Tsiper, West Lafayette, IN (US)

(73) Assignee: Maria V. Tsiper, West Lafayette, IN (US)

( * ) Notice: Subject to any disclaimer, the term of this patent is extended or adjusted under 35 U.S.C. 154(b) by 1932 days.

(21) Appl. No.: 10/840,537

(22) Filed: May 6, 2004

(51) Int. Cl.
*A61K 36/00* (2006.01)
*A61K 36/48* (2006.01)

(52) U.S. Cl. ........................................ 424/725; 424/757

(58) Field of Classification Search .................. None
See application file for complete search history.

(56) References Cited

U.S. PATENT DOCUMENTS

| | | | |
|---|---|---|---|
| 4,588,587 A | 5/1986 | Gasic | |
| 4,728,637 A | 3/1988 | Silverman | |
| 4,829,000 A | 5/1989 | Kleinman et al. | |
| 5,055,298 A | 10/1991 | Kludas | |
| 5,158,874 A | 10/1992 | Kleinman et al. | |
| 5,282,785 A | 2/1994 | Shapland et al. | |
| 5,346,897 A | 9/1994 | King | |
| 5,416,074 A | 5/1995 | Rabaud et al. | |
| 5,624,905 A | 4/1997 | Engvall et al. | |
| 5,762,909 A | 6/1998 | Uzgiris | |
| 5,830,910 A | 11/1998 | Mattson | |
| 6,117,862 A * | 9/2000 | Margaron et al. | 514/185 |
| 6,153,593 A | 11/2000 | Burgeson et al. | |
| 6,197,981 B1 * | 3/2001 | Liu | 549/510 |
| 6,284,284 B1 | 9/2001 | Naughton | |
| 6,300,367 B1 | 10/2001 | Taylor et al. | |
| 6,395,279 B1 | 5/2002 | Empire et al. | |
| 6,423,751 B1 | 7/2002 | Liao | |
| 6,465,001 B1 | 10/2002 | Hubbell et al. | |
| 6,497,906 B1 | 12/2002 | Kelly | |
| 6,569,841 B1 | 5/2003 | Holmberg | |
| 6,576,239 B1 | 6/2003 | Ruoslahti et al. | |
| 6,632,790 B1 * | 10/2003 | Yurchenco | 514/2 |
| 2002/0035074 A1 * | 3/2002 | Kelly | 514/27 |
| 2002/0193875 A1 | 12/2002 | Amano et al. | |
| 2003/0087985 A1 | 5/2003 | Hubbell et al. | |
| 2003/0152578 A1 | 8/2003 | Ruoslahti et al. | |

FOREIGN PATENT DOCUMENTS

| | | | |
|---|---|---|---|
| JP | 2003088329 A * | 3/2003 | |
| WO | WO 02/20723 A2 * | 3/2002 | |

OTHER PUBLICATIONS

Hatano et al., Phenolic comstituents of licorice. III. Structures of glicoricone and licofuranone, and inhibitory effects of licorice constituents on monoamine oxidase, Chemical & pharmaceutical bulletin, 39: 5: 1238-43, 1991.*
Berenbaum , Synergy, additivism and antagonism in immunosuppression, Clin Exp Immunol 28: 1-18, 1977.*
Sherratt et al, Mathematical modeling of cancer invasion, accessed on Aug. 27, 2009, pp. 1-4.*
Akashi T., et al.: Synthesis of basement membrane by gastrointestinal cancer cell lines. J Pathol., 187(2):223-8, 1999.
Akashi T., et al.: Reduced expression of laminin alpha 3 and alpha 5 chains in non-small cell lung cancers. Jpn J Cancer Res., 92(3):293-301, 2001.
An Y. and Hubbell J. A.: Intraarterial protein delivery via intimally-adherent bilayer hydrogels. J. of Cotrolled Release, 64: 205-215, 2000.
Birt D. F., Hendrich S., Wang W.: Dietary agents in cancer prevention: flavonoids and isoflavonoids. Pharmacol Ther. 90(2-3): 157-77, 2001.
Levitt M. L. and Koty P. P.: Tyrosine kinase inhibitors in preclinical development. Invest New Drugs.17(3): 213-26, 1999.
Liotta L. A. and Kohn E. C.: The microenvironment of the tumor-host interface. Nature 411, 375-379, 2001.
Woodhouse E.C., Chuaqui R.F., Liotta L.A.: General Mechanisms of Metastasis. Cancer Supplement 80 (8): 1529-37, 1997.
Tsiper M. V. and Yurchenco P. D.: Laminin assembles into separate basement membrane and fibrillar matrices in Schwann cells. J Cell Sci. 115(Pt 5):1005-15, 2002.
Tsiper M. V.: Basement membrane assembly on Schwann cell and myotube surfaces. Ph.D. Thesis, Rutgers University-UMDNJ, 2002.

* cited by examiner

*Primary Examiner* — Qiuwen Mi

(57) ABSTRACT

Methods and compositions for the prevention and/or treatment of metastatic cancer by tumor encapsulation achieved by introducing a physical obstacle to prevent cancerous cells from escaping the original site and invading other tissues. Physical obstacle is introduced as a pre-formed matter or its assembly by the treated organism is induced. In the preferred embodiment the composition of matter is disclosed, which enables formation of the obstacle in a form of basement membrane (BM). Said composition enables tissue cells to assemble BM on their surfaces, and supplies ECM components for said assembly, whereby BM is assembled de novo or the existing BM is strengthens. The composition comprises soy phytoestrogens, including genistein, daidzein, glycitein, biochantin A, and derivative thereof, actin cytoskeleton reorganization inhibitors, such as Cytochalasin D, and PTK inhibitors, in combination with ECM proteins, such as laminins and type IV collagens, or their derivatives.

7 Claims, 6 Drawing Sheets

Figure 4  Schematic Representation of the Process of *de novo* BM Assembly

Figure 6  *De novo* BM assembly upon Targeted Delivery of the Composition

TUMOR ENCAPSULATION FOR PREVENTION AND TREATMENT OF METASTATIC CANCER DISEASE

CROSS-REFERENCE TO RELATED APPLICATIONS

Not applicable

FEDERALLY SPONSORED RESEARCH

Not applicable

SEQUENCE LISTING OR PROGRAM

Not applicable

BACKGROUND OF THE INVENTION

Field of Invention

This invention relates to compositions and methods for prevention and treatment of metastatic disease associated with solid cancers.

BACKGROUND OF THE INVENTION

Stages of Cancer Progression

Solid cancerous (malignant) tumors represent localized masses of malignant cells and occur as devastating cancers of major organs such as lungs, kidney, breast, ovaries, skin, colon, prostate. Solid cancerous tumors are characterized by common stages of progression: appearance of a malignancy, proliferation, invasion, metastatic spread into other organs through the bloodstream or lymphatic vessels, insemination of new organs and massive proliferation at new sites. These stages can be grouped into pre-invasion, invasion and post-invasion stages. Pre-invasion stages are usually time-limiting. A solid tumor at pre-invasion stage, that is in situ, can exist and grow for a long time, sometimes for many years, with minimum discomfort to the patient. The disease often accelerates when the tumor becomes invasive, which is when the cancerous cells break through the normal tissue borders, causing normally suppressed mixing of cells from different tissue types (Liotta L. A. and Kohn E. C., 2001). At the invasion stage the disease usually progresses rapidly towards the metastatic disease when new tumors start to grow in other organs of the body. When the disease becomes metastatic it often progresses within months to lethality (Fidler I. J., 1997).

Treatments Aiming at Tumor Destruction

Various approaches have been developed to treat cancer at various stages of progression. The quality and availability of treatments reduce with advancing the stage. Modern medical methods are quite advanced at the level of diagnostics and allow for an early detection of the original tumor at the in situ stage, when the tumor causes little discomfort or none at all to the patient. However, our ability to treat diagnosed tumors is presently more limited and often inadequate to prevent deterioration of the disease into the invasive stage, at which time the effectiveness of known treatments reduces dramatically. Substantial fraction of known treatments aims at a selective destruction of the in situ tumor by means of chemotherapy, surgery or X-ray therapy. Even though an early-diagnosed tumors cause little discomfort to the patient, these standard destructive treatments are highly toxic or cause significant trauma and numerous adverse side effects, often resulting in disability. Once the cancer progresses into the invasive stage, there is no acceptably effective metastasis treatment known to date. The object of the present invention is to provide novel alternative treatment to delay or prevent tumor invasion.

Chemotherapy relies on medicines that are more poisonous to the malignant cells than to the normal cells with the aim at destroying completely the former while sparing the later. An essential difficulty is that the distinction between the normal and malignant cells is often minute, and most chemotherapeutic agents do not achieve complete differentiation. In essence, the hope is for the substance to poison the tumor before it poisons the patient.

Surgery remains by far the most effective way of treatment of non-metastatic solid tumors, though it is not always available as an option. In addition to the risk of regular surgical complications, cancer surgery carries a risk of metastatic insemination due to the left-behind malignant cells, and due to the tissue damage contributing to pathways for cancer invasion. Therefore, modern medical procedures recommend cycles of after-surgery chemotherapy, which again involve serious side effects, long-term disability and expensive medications.

Alternatives to Destructive Treatments. Anti-Invasion Treatments.

One of the most prospective approaches in today's cancer research, alternative to the tumor destruction, is prevention of cancerogenic invasion by tumor in situ. Prior art in this area is the recent development of the whole new class of anti-tumor therapeutic agents that inhibit angiogenesis and extracellullar matrix (ECM) degradation.

ECM degradation is the key element in the mechanism of cancer invasion. ECM is a complex organized structure filling the space between individual cells comprising a tissue. ECM serves important purposes of intercellular communication, maintaining structural integrity of the tissue, regulating cell mobility and cell migration within the tissue. As such, ECM is the natural guard against tumor invasion.

In order to invade, cancerous tumors are known to actively attack the ECM, degrading its components and structure, and reducing its anti-invasive potential. Furthermore, ECM degradation liberates growth factors, which promote angiogenesis and further tumor growth, thereby facilitating and accelerating tumor progression and invasion.

A class of cancer treatments is antiangiogenic treatments which aim at the inhibition of angiogenesis that is the disruption of tumor blood supply. Antiangiogenic agents prevent new blood vessel formation and disrupt the tumor blood supply that is necessary for tumor growth. Many therapeutic candidates that inhibit angiogenesis are currently under clinical trials (reviewed by Lafleur M. A., et al., 2003). The action of angiogenic inhibitors is based on:
- the blockage of angiogenic signaling stimuli such as the vascular growth factor (VGF) receptors;
- the use of matrix metalloprotease inhibitors (MMPI) to inhibit of ECM proteolysis (degradation), which causes the release of the growth factors located within ECM.

VGFs (such as VEGF, FGF or EGF) are small, secreted molecules that stimulate cell signaling through the specific membrane receptors and are required for functional vessel formation (Yancopoulos G. D., et al., 2000). Many growth factors that promote angiogenesis are located in ECM and are released upon the ECM breakdown. Current drug design aims at the specific blockage of receptor-ligand binding and signaling or selective inhibition of gene expression. The examples are Platelet Factor 4 (PF-4) and PF-4-derived synthetic peptides, which inhibit functions of FGF-2 and VEGF by preventing binding to the corresponding receptors (Jouan V., et al., 1999). SU5416 inhibits the tyrosine kinase activity of VEGFR-2 (Mendel D. B., et al., 2000). Angiozyme selectively inhibits the expression of VEGFR-1 by cleavarage of its mRNA (Sandberg J. A., et al., 1999).

MMPIs are inhibitors of enzymes, named matrix metalloproteases (MMPs), which are capable of degrading components of the ECM, in particular basement membrane and stromal ECM. ECM breakdown causes (i) release of angiogenic factors and (ii) destruction of a the vital barrier for metastatic spread. MMPIs thus prevent ECM degradation by MMPs and the release of ECM-contained growth factors that regulate angiogenesis (Liotta L. A., et al., 1991; Stetler-Stevenson W. G., et al., 1993). In physiological conditions there is a balance between the activity of MMPs and the expression of their natural inhibitors (tissue inhibitors of metalloproteases, or TIMPs). However, in pathological conditions this equilibrium is lost. Recent studies have revealed that cancers often have high levels of expression of MMPs that are secreted by many cancerous cells (Wojtowicz-Praga S. M., et a, 1997; Birkedal-Hansen H., 1995). Based on these findings, natural TIMPs are suggested to be an attractive group of anti-cancer therapeutics (Ikenaka Y., et al., 2003, Li H., et al., 2001). Moreover, several synthetic MMP inhibitors have been developed and are presently being studied in clinical trials as candidates for anti-cancer therapeutics. Among them are Prinomastat or AG-3340 (Shalinsky D. R., et al., 1999), Neovastat or AE-941 (Gingras D., et al., 2003), Batimastat (BB-94), Marimastat (BB-2516), COL-3, Bryostatins (Coussens, L. M., et al., 2002; Drummond A. H., et al., 1999).

Further, it is known that fragments of ECM proteins often possess an ability to inhibit angiogenesis by interfering with cellular adhesion, migration, and proliferation. Several new anti-angiogenic drugs currently undergo clinical trials; among them are Arrestin, Canstatin and Tumstatin which are fragments of type IV collagen (Maeshima Y., et al., 2002; Maeshima Y., et al., 2000; Colorado P. C., et al., 2000; Kamphaus G. D., et al., 2000). Laminin1-derived peptides have been shown to possess anti-angiogenic properties (Ponce M. L., et al., 2003). Laminin peptides and derivatives thereof were suggested to use in cancer treatment and are covered by U.S. Pat. No. 5,211,657 (Yamada Y., et al., 1993) expressly incorporated herein by reference.

Current Issues

Present methods are clearly insufficient to prevent or treat the metastatic cancer disease. Cancerous tumor invasion, followed by the metastatic cancer disease, is the major cause of failure of the currently available cancer therapies.

Chemotherapeutic treatments are highly toxic due to limited ability to differentiate between malignant and normal cells. Chemotherapy does not directly prevent cancerous invasion, which leads to metastatic disease.

Destructive treatments, such as cancer surgery, also do not directly prevent cancerous invasion and may, in fact, even facilitate the invasion by contributing to the invasion pathways.

The known methods for prevention of cancer-induced ECM degradation target only specific mechanisms of ECM degradation, such as inhibit MMPs, while there may be other mechanisms for the ECM degradation. In addition, these methods completely lack an ability to undo the damage to ECM that has already been done, but can possibly only slow down the degradation process.

No effective treatments are known to target cancer invasion as such.

The purpose of this disclosure is to provide a completely different approach to prevent cancerous invasion by solid tumors.

BACKGROUND OF THE INVENTION

Objects and Advantages

The main object of this invention is to provide new means to target directly the cancerous tumor invasion, thereupon preventing or significantly delaying the ensuing metastatic disease. The idea of the present invention is to introduce a physical obstacle, or barrier, between the tumor and the healthy tissue. Such a physical obstacle is to prevent the malignant cells from the tumor to migrate (travel, drift, diffuse) into the healthy tissue, blood or lymphatic vessels, thus reducing the tumor invasion potential. As a result, the original tumor mass remains intact and no insemination of nearby tissues occur, or such insemination is reduced or limited. The metastatic disease is thereby prevented or its onset is significantly delayed.

Said physical obstacle can be introduced in a multitude of ways. In the preferred embodiment said physical obstacle is introduced in a form of the basement membrane, either natural or artificially assembled on certain cell surfaces. Basement membrane (BM) is a cell-associated part of ECM that has a specific molecular composition and structure (Alberts B., 1994). BM separates different cell types, contributes to structural integrity of tissues, and as such plays the role of a natural barrier against tumor invasion. In this preferred embodiment the objective is achieved by means of strengthening or de novo assembly of BM on the surface of cells in a living tissue, in particular in the proximity of the tumor, as a result of treating the cells with a certain disclosed composition.

The disclosed invention has several key advantages against presently known cancer treatments. First, the method is non-destructive, and is likely to pose significantly less danger to health of the patient, compared to conventional destructive treatments, such as chemotherapy, X-ray therapy or surgery. Instead of the destruction of the existing tumor(s), the method attempts to prevent or to delay the invasion (spread) of the tumor(s) to other tissues, which is usually the most damaging effect of cancer.

Second, the invention takes a new and largely unexplored route in cancer therapy, and therefore may supplement the efficacy of the existing treatments, can be provided concurrently with other treatments, or can be applicable where other treatments are not available. The early-diagnosed in situ tumor is encapsulated within the obstacle and its progression to the invasion phenotype is prevented or delayed. Cancerous cells or healthy cells in the surrounding of the tumor are trained to assemble BM on their surface, thus leading to tumor encapsulation within the de novo formed BM, preventing insemination of other tissues. After-surgical recurrence of cancer due to residual left-behind malignant cells is prevented or delayed by re-assembly of the BM damaged in the course of the surgery.

Third, the method is not tumor-specific and can be applied to various types of solid tumors. Unlike the methods that target ECM-degrading agents, the present method strengthens or assembles the basement membrane, essentially regardless of the way it is being or has been degraded. Tumor-specific aspects are limited to possibly defining specific area of application, such as targeted delivery of the agent to the area of the tumor.

Further, the method has a healing character. For example, unlike known treatments, it is able to undo the damage to the basement membrane that has already occurred before therapy due to the tumor growth or other causes. Instead of suppressing the tumor-induced ECM degradation by means of targeting specific pathways, this invention aims at strengthening and/or de novo formation of the basement membrane, thus leading to the same goal of strengthening anti-invasion barriers.

Moreover, the method can be beneficial if applied to healthy people with prophylactic purposes, particularly to people with predisposition to cancer, or those who underwent surgery to remove cancerous tumor(s).

Lastly, the disclosed compositions are based partly on natural compounds, such as soy isoflavones, which are readily available as nutritious supplements. Soy isoflavones have been suggested as compounds with positive anti-cancer effects. Methods of isoflavones purification and concentrations of use are covered by U.S. Pat. No. 6,395,279 (Empie M., et al., 2002) and U.S. Pat. No. 6,497,906 (Kelly G. E., 2002) referred herein as examples. Purified components of basement membrane have been used previously as means of improving skin condition or to repair skin basement membrane damage, as disclosed in U.S. Pat. No. 5,055,298 (Kludas M., 1991) and U.S. Pat. No. 6,153,593 (Burgeson R. E., et al., 2000) referred herein as examples. However, such compounds have never been used within the disclosed composition. The disclosed composition achieves a key new effect by turning the cells of living tissue into basement-membrane competent cells, which actively assemble basement membrane on their surface.

This invention is based on the recent experimental data obtained by the inventor [Tsiper M. V., 2002; Tsiper M. V. and Yurchenco P. D., 2002], who found the ways to manipulate cell competency with respect to BM assembly. Thus, an objective of assembly or strengthening of BM on the surface of living cells can be achieved.

SUMMARY

The present invention provides methods and compositions for treatment and prevention of metastatic cancer disease in individuals who have been diagnosed with cancer, or have predisposition to cancer, or underwent surgery to remove cancerous tumor(s). The present method targets directly the invasion (spread) of the existing tumor(s) to other tissues and organs and ensuing metastatic disease, in order to prevent or delay the onset of the metastatic disease. The key element of the invention is a physical obstacle, or barrier, introduced in the proximity of the tumor to reduce the tumor invasion potential and cause tumor encapsulation.

Physical obstacle as referred herein is a material entity extended in at least two dimensions, either artificial (such as a polymer) or natural (e.g. composed of biological tissue or parts thereof, such as basement membrane). Said physical obstacle is either formed de novo, or strengthened when it already exists.

Tumor encapsulation as referred herein is either de novo formation or strengthening of an existing physical obstacle in the proximity of the tumor, whereby the tumor invasion potential is reduced.

Partial encapsulation is referred herein as a tumor encapsulation where said physical obstacle is introduced in specific areas with respect to the tumor, so that the tumor spread in a certain, most critical direction is delayed or prevented.

Said physical obstacle can be either completely impermeable for certain cell types, or have the permeability below a predetermined value (such as, e.g. collagen sponge). Irrespective of the cell permeability, said physical obstacle can be either permeable, impermeable, or semi-permeable for chemical substances and/or water.

Said physical obstacle can assume a multitude of forms. In the preferred embodiment an ECM part named basement membrane (BM) plays the role of said physical obstacle. BM is a cell-associated part of ECM that has a specific molecular composition and structure, and poses a natural obstacle for tumor invasion.

Formation, strengthening or stabilization of BM, in particular in the proximity of tumor(s), has a goal of formation, strengthening or stabilization of physical obstacle against tumor invasion, thus preventing or significantly delaying the onset of the tumor invasion and the ensuing metastatic disease. This invention discloses methods and compositions for promoting stabilization, strengthening and/or de novo formation (assembly) of BM on the surface of cells in vivo (in a living tissue), particularly the malignant cells, or other cells in the proximity of the tumor(s). In particular, this invention discloses methods and compositions for manipulating the cells in vivo in such a way as to promote an active assembly of the BM by the treated cells.

BM referred herein is BM in the tissues relevant for tumor invasion, such as blood or lymphatic vessels, BM in breast, colon, rectum, lung, oropharynx, esophagus, hypopharynx, stomach, pancreas, liver, gallbladder and bile ducts, small intestine, urinary tract, (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), skin or other tissues significant for specific cancers.

BM formation (assembly) as referred herein is a complex cell-associated process which occurs on the surface of certain live cells under certain conditions.

BM competency as referred herein is the set of conditions, which cause live cells to assemble BM on their surfaces. One of the conditions (necessary, but generally not sufficient) for the BM formation (assembly) is the availability of certain concentrations of ECM components. Said ECM components may be either endogenously available or supplied as a part of the proposed composition.

BM stabilization as referred herein is the reduction of the rate of the process of BM degradation, including complete cessation of BM degradation.

BM strengthening as referred herein is the process in which the structure of an existing BM improves in terms of density, structure quality or coverage of the cell surface. This particularly includes, but is not limited to BM that has been degraded (weakened) due to a prior damage or disease. BM strengthening occurs in two ways, initiated either by the cell, or initiated extracellularly.

Further aspects of the invention are made apparent by the supplied drawings and the following description of preferred embodiments of the invention. The details of the invention can be modified in a number of respects, all without departing from the inventive concept, whose key element is to introduce a physical obstacle against tumor invasion. A person skilled in the art will realize that other embodiments of the invention are possible, in particular in the multitude of forms said physical obstacle can assume. Thus, the following drawings and description are to be regarded as illustrative in nature and not restrictive.

DRAWINGS

Figures

The features of the invention will be better understood by reference to the accompanying drawings which illustrate the invention.

The figure illustrates the main idea of introduction of a Physical Obstacle. Early-diagnosed tumor (dark blue cells) is prevented from spread and/or interaction with healthy cells (light blue) by the physical obstacle (red line). Tumor cells are encapsulated either fully (left) or partially (right). In case of full encapsulation tumor is surrounded by the Physical Obstacle. In case of partial encapsulation the Physical Obstacle is introduced in certain area preventing tumor spread in most critical direction.

The figure illustrates processes (a-d) that lead to major stages of cancer disease progression. (a) Cancerous cell (dark), once developed proliferate relentlessly and occupy regions normally occupied by other cells (light circles). (b) The next stage, the beginning of true malignancy, occurs when tumor cells degrade ECM, cross the BM and invade the underlying connective tissue. (c) In order to metastasize in distant organs tumor cell must enter the circulation, i.e. to invade blood or lymphatic vessels crossing through the BM and endothelial lining of the vessel. (d) The final process in metastatic disease progression is characterized by tumor cells invasion of distant tissues (light squares) and appearance and growth of metastases.

The progression of nearly appeared tumor into the metastatic disease is prevented at different stages by the introduced Physical Obstacle (thick line). (a-d) represent same processes of cancer progression as in FIG. 2. BM introduced as a Physical Obstacle at each particular stage prevents (or delays) the consecutive stages of disease progression. (a) BM, encapsulating the tumor at the stage of its uncontrolled growth, prevents (or delays) the spread of cancerous cells to the areas occupied by normal (healthy) cells (light). (b) BM at the tissue interface prevents or delays the degradation of ECM and connective tissue invasion. (c) BM of blood and lymphatic vessels, i.e. lumen BM, prevents or delays cancerous cells entry the circulation. (d) BM of distant (healthy) tissues prevents (or delays) cancerous cells from invasion and insemination of distant healthy tissues and the ensuing metastatic disease.

BM formation from structural BM components is allowed only on specific, BM-competent cell surfaces. Disclosed composition provides means for enabling BM-competency (e.g. genistein) along with structural BM components (e.g. laminin). Upon treatment with the composition BM-incompetent cells gain competency to form the BM. BM-competent cells then form the BM on their surface from the BM structural components supplied with the composition or available endogenously.

In order to invade other tissues and metastasize cancerous cells of a solid tumor induce degradation of the existed BM. BM degradation leads to the insemination of other tissues and development of metastatic disease. Treatment with the disclosed composition strengthens the existing BM and thus prevents tumor invasion.

Cancerous cells may escape the original solid tumor mass, migrate and form new tumors. When disclosed composition is targeted to be delivered to cancerous cells it induces the formation of the de novo BM on tumor mass interface, thus encapsulating the tumor and preventing individual cancerous cells from migration.

DETAILED DESCRIPTION

The following section is provided by way of background to better appreciate the invention.

Figure 1A:
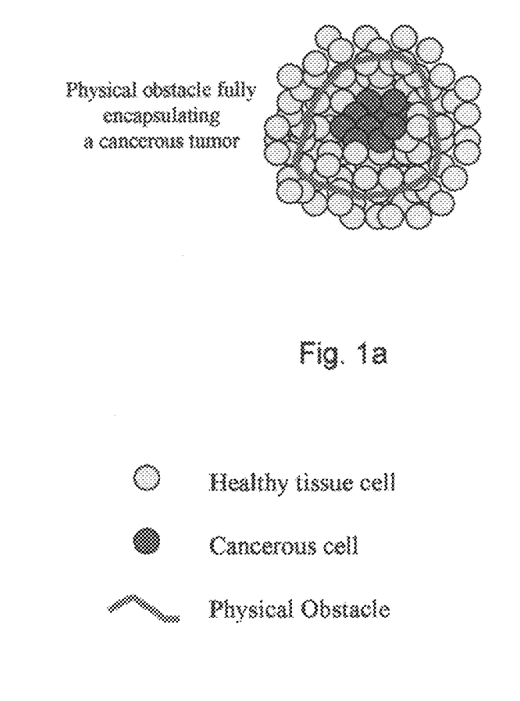
FIG. 1. Tumor Encapsulation with a Physical Obstacle.

FIG. 1 illustrates the key element of the invention. Said physical obstacle encapsulates the tumor fully or partially, whereby invasion of other tissues is prevented or delayed. Said obstacle is either introduced (assembled) de novo, or a pre-existing obstacle is enhanced (strengthened). For example, breast carcinoma of breast is characterized by the proliferation of malignant epithelial cells within lobules or ducts surrounded by a BM which is normally intact while the tumor is in the in situ stage of progression. BM integrity is compromised during the invasion stage. Strengthening of said BM results in said physical obstacle fully encapsulating said in situ tumor, preventing or delaying tumor invasion. As sketched in FIG. 1(a), said physical obstacle need not be located at the exact boundary of the tumor. In the above example of breast cancer, said BM separates two types of tissues, one of which may contain both cancerous and healthy cells.

Figure 1B:
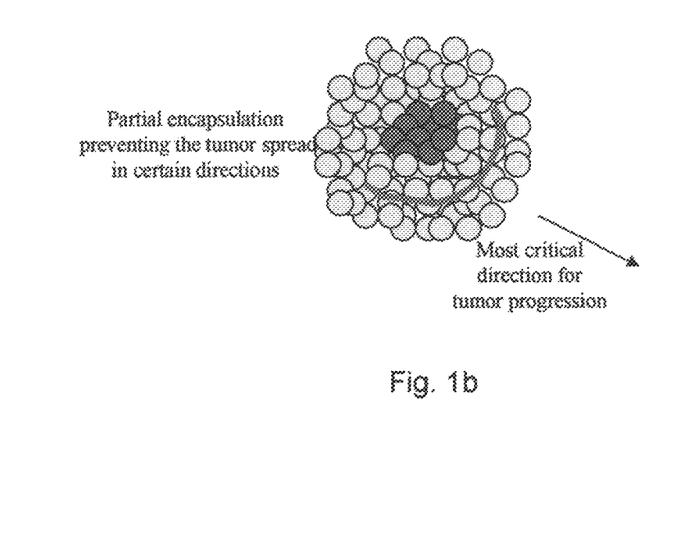

FIG. 1(b) sketches a situation of partial tumor encapsulation, where a potential spread of said tumor is prevented in the most critical directions, thus channeling said spread into areas where the least damage from said spread will result. For example, melanoma progression to the deepest layers of dermis and underlying tissues can be delayed or prevented by incorporation of a physical obstacle placed between dermis and epidermis. The skin has three layers: epidermis (most external), dermis, and subcutis. BM separates the epidermis from the deeper layers of skin. Melanoma originates from melanocytes, cells that are localized in the epidermis, and becomes life-threatening after breaking through the BM and invasion into the dermis. Incorporation of a physical obstacle that separates the dermis from epidermis shall prevent melanoma invasion.

Figure 2:
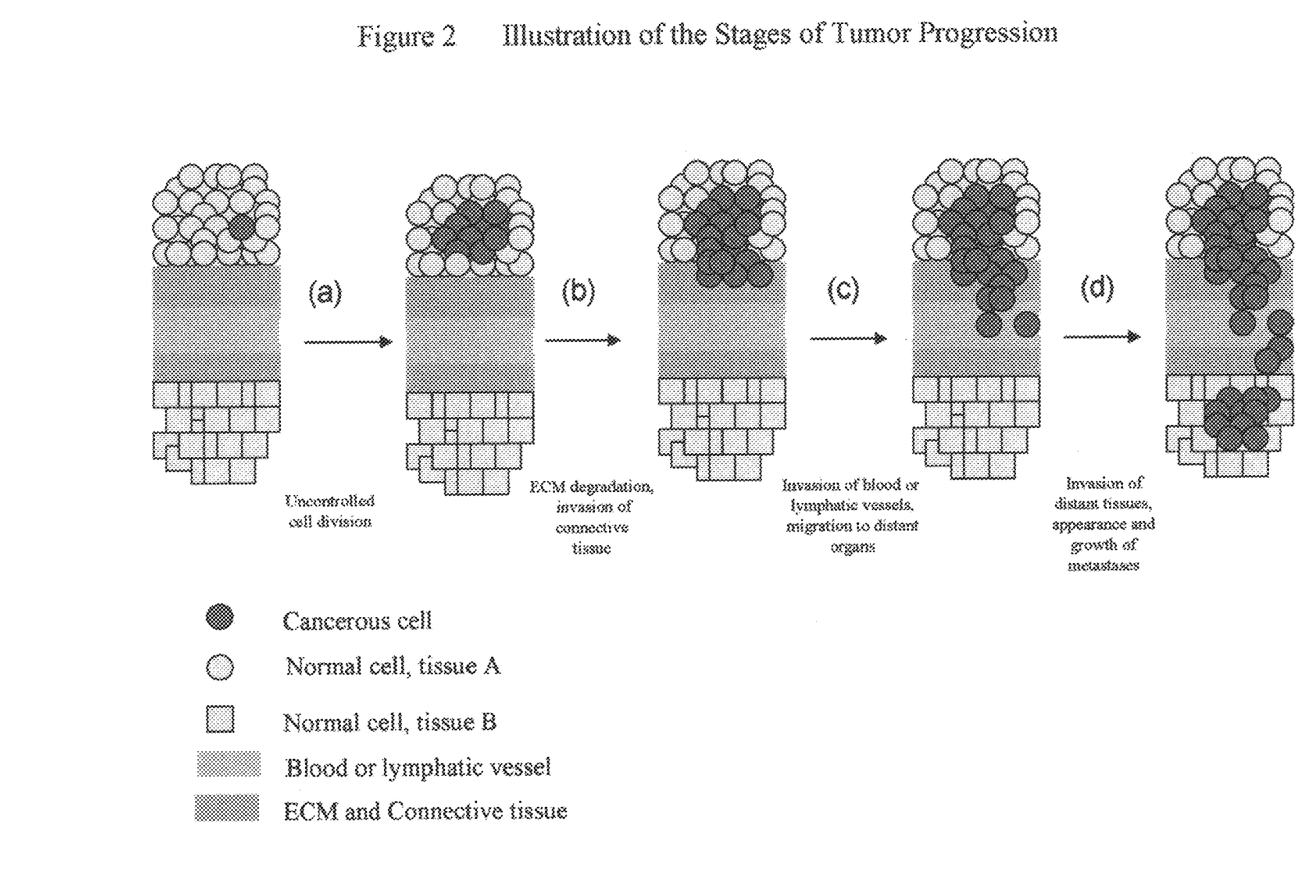
FIG. 2. Illustration of the Stages of Tumor Progression.
Figure 3:
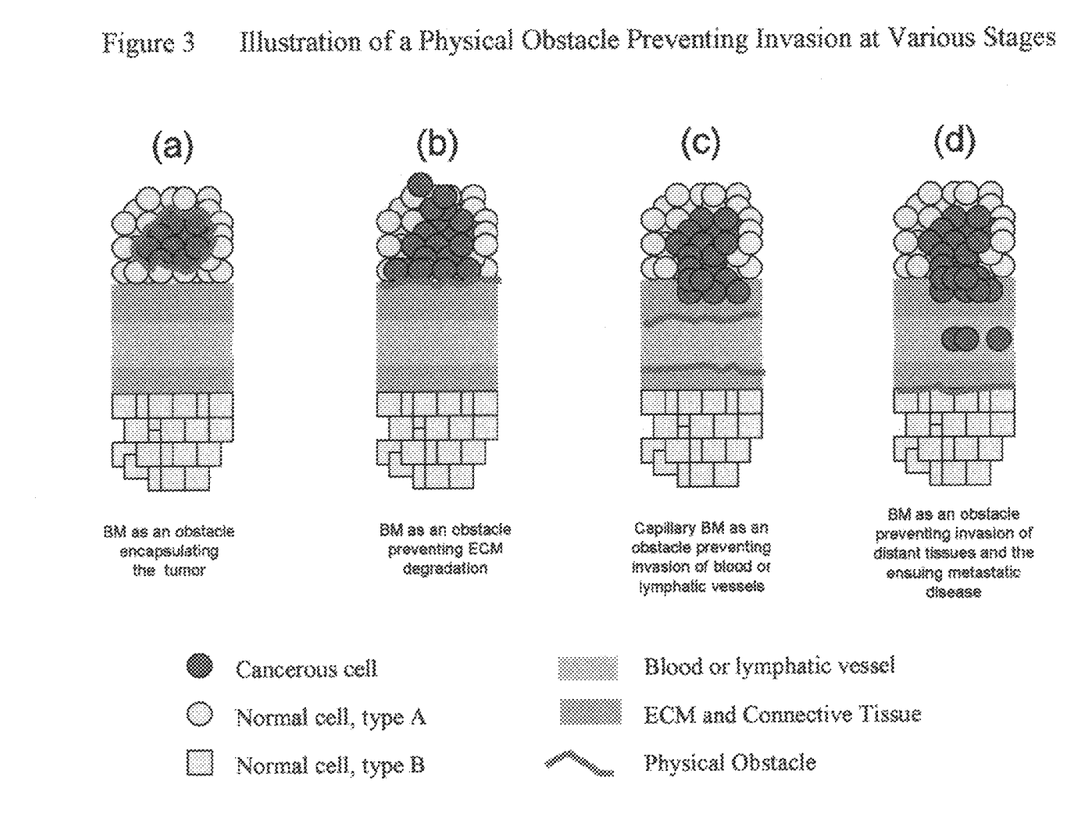
FIG. 3. Illustration of BM as a Physical Obstacle Preventing Invasion at Various Stages.
Figure 4:
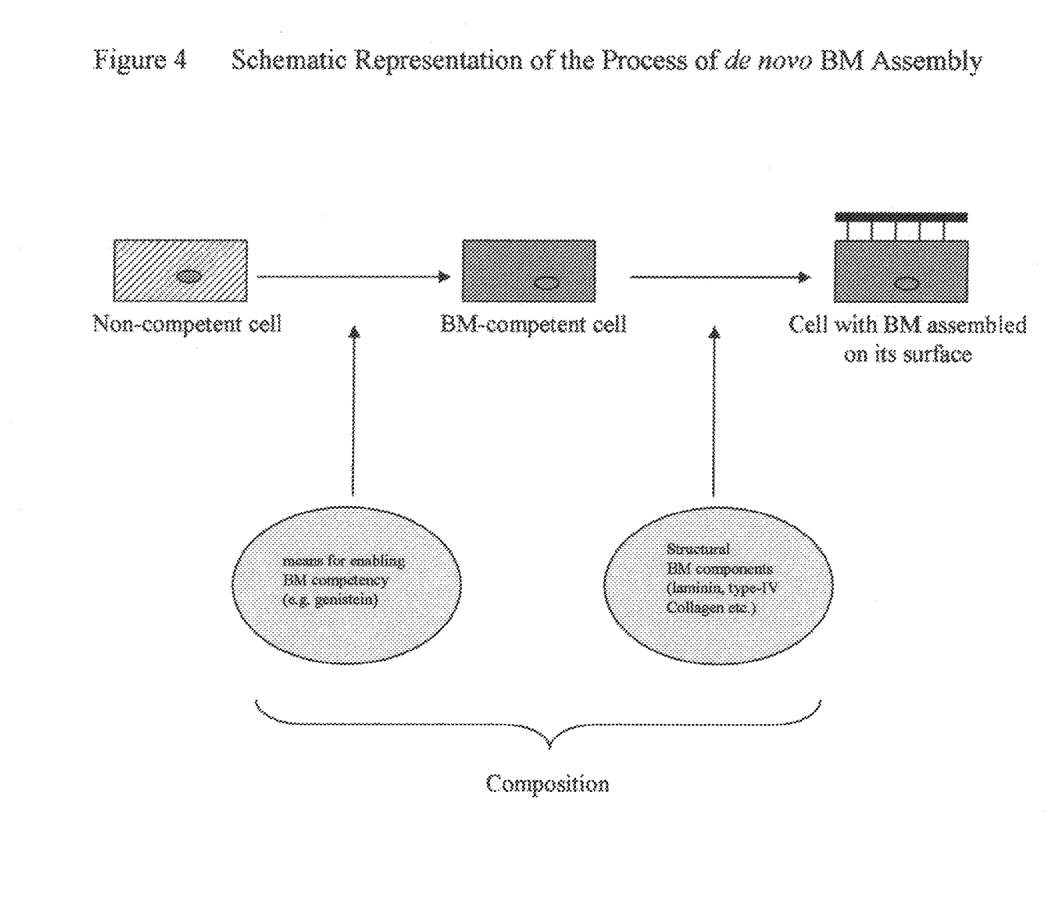
FIG. 4. Schematic Representation of the Process of de novo BM Formation.
Figure 5:
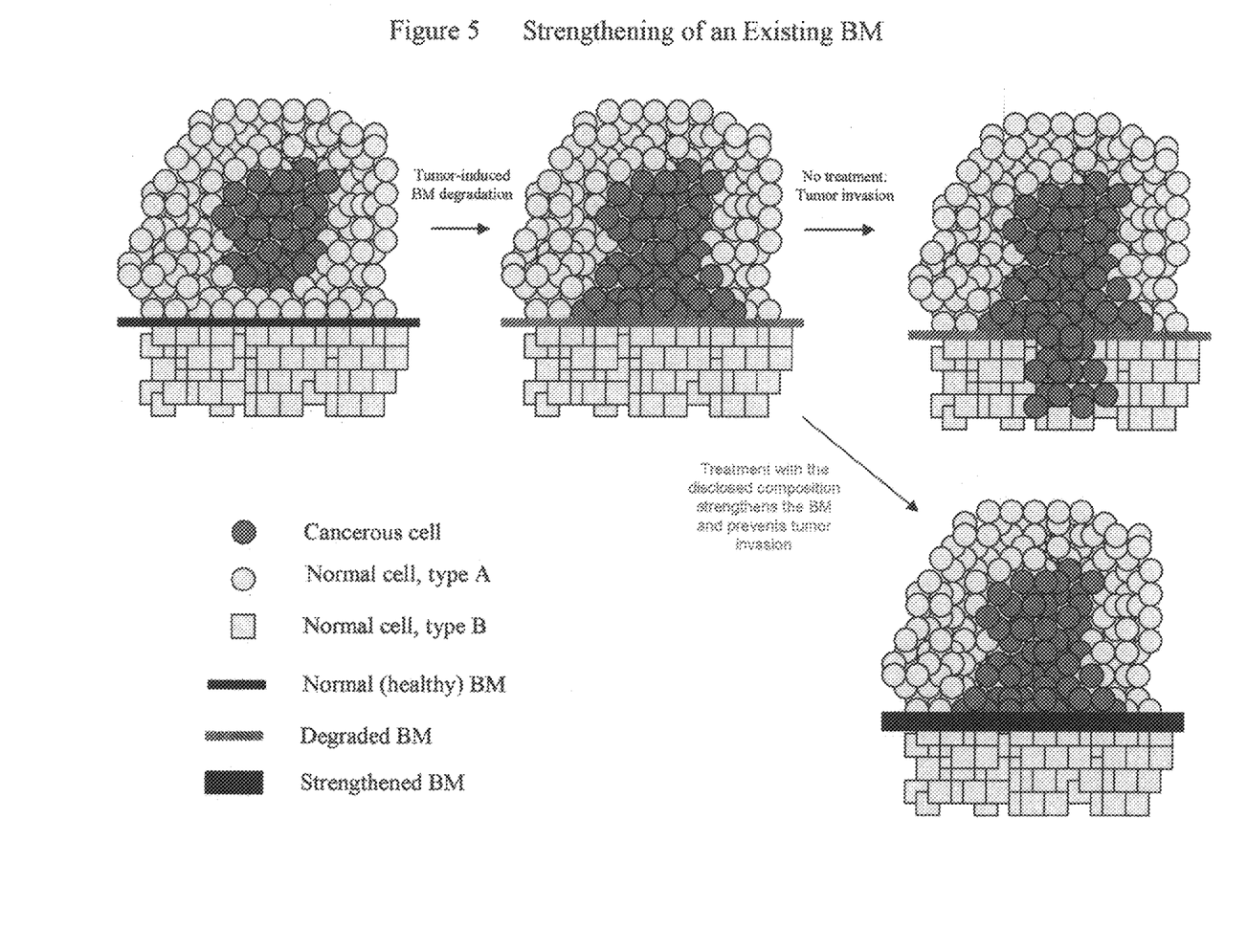
FIG. 5. Schematic Representation of the Process of Strengthening of an Existing BM.
Figure 6:
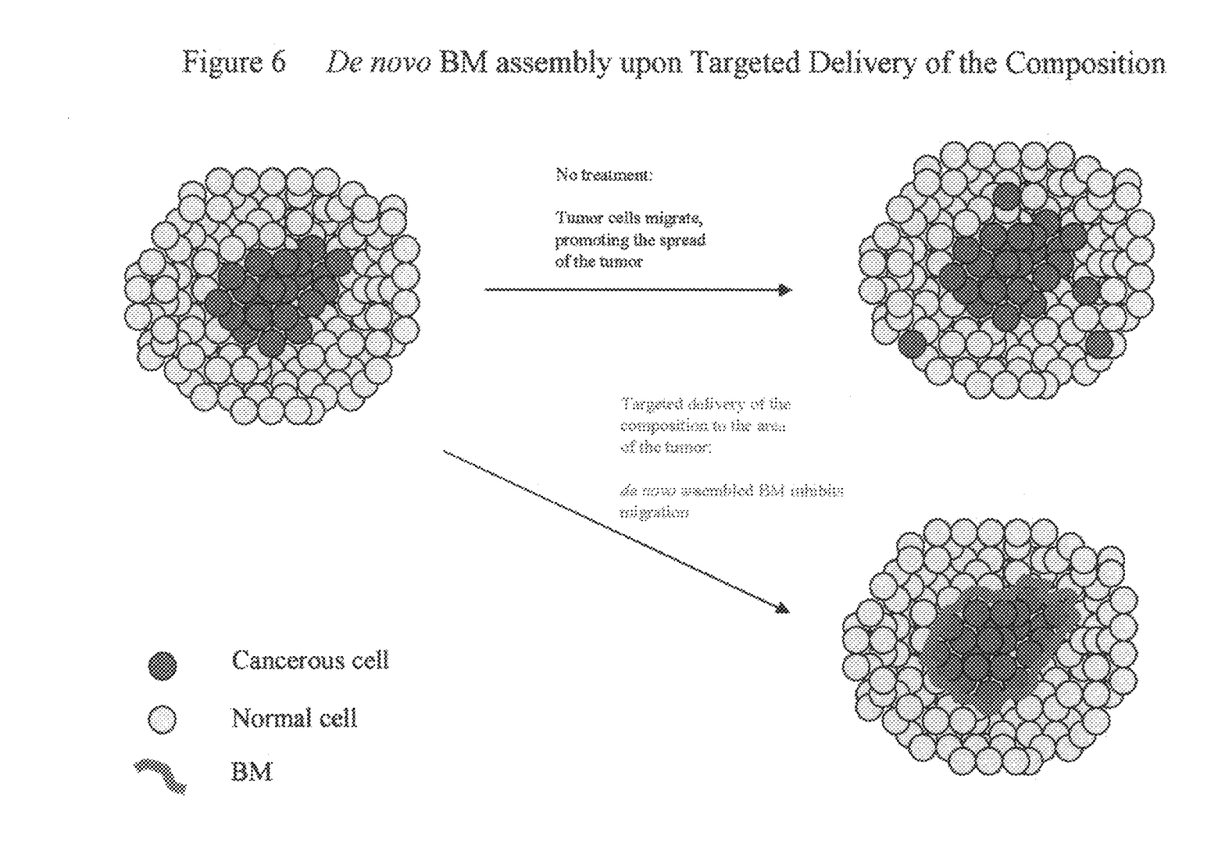
FIG. 6. De novo BM Formation upon Targeted Delivery of the Composition.

Placement (localization) of said physical obstacle may depend on the specifics and stage of the disease progression (FIGS. 2 and 3). Briefly, uncontrolled division of a cell leads to the tumor growth and occupation of areas normally reserved for healthy cells. Tumor is referred to as in situ until the cancerous cells break through the BM separating two types of tissue cells and invade the connective tissue. The next critical step is the invasion of blood or lymphatic vessels by crossing through their BM and endothelial lining. With the circulation of body fluids some cancerous cells travel throughout the body, break through the vessel wall and invade distant tissues, such as liver, lungs, brain, etc. FIG. 3 illustrates benefits of a physical obstacle introduced at various locations: (a) full encapsulation at the in-situ stage works towards keeping the tumor mass intact; (b) partial encapsulation prevents the invasion of the connective tissue; (c) a physical obstacle lining the capillary walls prevents migration of the malignant cells into the blood or lymphatic vessel; (d) similar lining of distant capillaries prevents insemination of distant tissues by the malignant cells transported through the blood or lymphatic vessels. A person skilled in art will find the optimal localization of the obstacle depending on the stage of the disease, origin of the tumor, possibilities of surgical treatment, availability of therapeutics, etc.

Preferred Embodiment

In the preferred embodiment said physical obstacle against tumor invasion is realized in the form of basement membrane (BM). BM is a protein based cell-associated part of ECM that separates tissue cells from underlying or surrounding connective tissue. BM is present in nearly every organ and has a common structural appearance of a thin (50-200 nm) mat and a tissue-specific molecular composition and structure. BM represents a natural barrier against tumor invasion since the invasion is usually accompanied by structural changes in the BM structure, as observed in many types of human cancer, such as gastrointestinal cancer and lung cancer (Akashi T., et. al., 1999; Akashi T., et. al., 2001), oral cancer (Wilson D. F., et al., 1999). BM penetration by cancerous cells is a critical step in tumor invasion and the development of metastatic disease. Usually cancerous cells have to pass through several BMs in order to metastasize in other organs.

Assembly of said BM is enabled upon treatment with a composition of matter comprising (i) means for enabling BM competency of tissue cells and (ii) one or more structural BM components or derivatives thereof. Said means for enabling BM competency can be realized in a multitude of ways, several of which are disclosed below as (1) one or more phytoestrogenic isoflavones (such as genistein, daidzein, glycitein, formomometin, and biochanin A), (2) one or more actin cytoskeleton perturbing agents (such as Cytochalasin D, colchicin, myosin light chain kinase inhibitor, myosin light chain phosphatase, protein kinase N inhibitor, phospatidylinositol 4-phosphate 5-kinase inhibitor), (3) one or more phospho-tyrosine kinase inhibitors, or (4) a combination of some or all of the above. Examples of structural BM components are laminin, type IV collagen, nidogen and HSPG.

(i) Means for Enabling BM Competency

Said phytoestrogenic isoflavones, in particular soy-derived isoflavones, are used in this embodiment as means to manipulate tissue cells in such a way as to enable the mechanism of assembly BM by said cells on their surfaces. For example, genistein has been found to promote BM competency in cell cultures of differentiated myotubes and glial Schwann cells (Tsiper M. V., 2002).

Many population studies drew overall attention to a potential anticancer effect of soy-containing diets (reviewed in Birt D. F., et al., 2001). It is well known that Asian people have lower frequency of cancer, whereas people of Asian descent who reside in the U.S. become more susceptible to this disease. This fact points towards relevance of Asian diets, known to have significant soy content. Population studies show that individuals who consume significant amounts of soy in their diets have lower rates of occurrence of prostate and breast cancer (Lee M. M., et al., 2003; Wu A. H., et al., 2004; Wu A. H., et al., 2002). Soy diets have been recorded as potentially favorable in the prevention of breast, colon, prostate, stomach and lung cancers. Many soy components are patented in respect to cancer prevention, however no effective soy-based therapeutics have been developed so far. Soybeans are known to contain at least five families of compounds with anticancer activity. Soy isoflavones is one such family, versatile and potent effects of which have been the focus of cancer research. Said soy isoflavones, especially genistein and daidzein, are known to inhibit cancer cells proliferation, for example human breast cancer cells (Monti E., et al., 1994).

Soy isoflavones are not harmful for consumption, and are available in stores as a dietary supplement. Genistein (5,7,4'-trihydroxyisoflavone), an isoflavone, is a naturally occurring tyrosine kinase inhibitor abundant in soybeans and tofu. Genistein is available commercially as a chemical, e.g. from Calbiochem (La Jolla, Calif.), and as a dietary supplement, e.g. from eVitamins (MI, U.S.). Alternately, genistein can be prepared by fermentation (Ogawara H., et al., 1986). Genistein can be conjugated with cancer-specific molecules like EGF for targeted delivery as disclosed in U.S. Pat. No. 5,911,995 (Uckun F. M., 1999) incorporated herein by reference.

Said actin cytoskeleton perturbing agents are used in this embodiment as another means to manipulate tissue cells in such a way as to enable the mechanism of assembly BM by said cells on their surfaces. Said agents are selected, for example, from a group consisting of myosin light chain kinase inhibitor, myosin light chain phosphatase, protein kinase N inhibitor, phospatidylinositol 4-phosphate 5-kinase inhibitor, colchicin, cytochalasin D, or other agents that disrupt actin cytoskeleton organization. The exemplified preferred agent that disrupts actin cytoskeleton organization is cytochalasin D, which is available commercially under that name (e.g. from Sigma-Aldrich Co., MO, U.S.).

Cytoskeleton as referred herein is the protein network composed of actin filaments and microtubules in the cytoplasm of a living cell, which is responsible for cell shape, movement and transport of intracellular constituents. BM is linked with the cytoskeleton through a complex of membrane receptors and proteins. BM formation is initiated by laminin interaction with said membrane receptors and polymerization-dependent laminin-based nascent BM (Colognato H., et al., 1999). Thus, laminin-based nascent BM formation is mediated through the membrane receptors, in particular by their availability and lateral mobility in the plane of the membrane, which in turn is affected by the cytoskeleton organization. Moreover, agents that interfere with cytoskeleton rearrangements are believed to prevent BM disassembly on cultured C2C12 myotubes (Tsiper M. V., 2002). Intracellular rearrangements of cytoskeleton cause re-localization of receptors in the membrane plane, preventing or destructing laminin polymerization on the membrane surface, thereby preventing BM formation.

Said phospho-tyrosine kinase inhibitors are used in this embodiment as yet another means to manipulate tissue cells in such a way as to enable the mechanism of assembly BM by said cells on their surfaces. Tyrosine kinases are associated with many regulatory cellular processes. Their role in oncogenesis is broadly accepted. A multitude of tyrosine kinases are upregulated in human cancers, for example, HER-2/neu is overexpressed in breast cancer, EGFR in glioblastoma, Src in colon and breast cancer, and Rsc/Sky in breast cancer.

A multitude of phospho-tyrosine kinase inhibitors can be used for the purpose of this invention, as reviewed below. To-date, several successful agents have been developed, some of which are in clinical trials (for review see Al-Obeidi and Lam, 2000). For example, Herceptin, which is a monoclonal antibody against the extracellular domain of Her-2/neu (Baselga J., 2001; Stebbing J., et al., 2000) has been proven successful for Her-2 positive breast cancer therapy. Classes of protein tyrosine kinase inhibitors also include quinazolines, pyridopyrimidines and related heterocyles, phenylamin-pyrimidines, benzylidene malonitrile (tyrphostins and their analoges), and indoles and oxindoles (for review, see Levitt M. L. and Koty P. P., 1999; and Al-Obeidi F. A. and Lam K. S., 2000). Interestingly, some phytoestragenic isoflavones, like genistein, possess the activity to inhibit protein tyrosine kinases as well.

In recent years, combinatorial libraries have been assembled and screened for beneficial compounds with kinase inhibitor activities. High-throughput assays have been utilized for screening protein kinase inhibitors, including the fluorescence polarization assay (Seethala R. and Menzel R., 1998), the scintillation proximity assay and the time-resolved dissociation-enhanced fluorescence technology (Braun-walder A. F. et al., 1996). Furthermore, computational chemistry has been used increasingly for development of protein kinase inhibitors, particularly with the recent increase in the number of available crystal structures and with progress achieved in structure-based drug design (for review, see Al-Obeidi F. A. and Lam K. S., 2000). Peptide substrates for numerous protein tyrosine kinases have also been identified. Potent inhibitors have been developed for protein kinase A based on modifying the components of a particular peptide substrate (Glass D. B., et al., 1995), and similar approaches have been utilized for protein tyrosine kinases (for example, Alfaro-Lopez J., et al., 1998).

(ii) Structural BM Components

Said structural BM components are used in the disclosed compositions to provide the material components to assemble BM on the surface of BM-competent cells. Said structural BM components are one or more ECM proteins from the group of laminin, type IV collagen, nidogen, heparan sulfate proteoglycan (HSPG), and their derivatives. Said proteins are commercially available, e.g. Cultrex® BM proteins from Trevigen, Inc., MD, U.S.

Laminin is one of the major BM structural proteins and is known to induce assembly of primary laminin-based BM on BM-competent cell surfaces, such as on in vitro differentiated C2C12 myotubes (Tsiper M. V., 2002), and on cultured primary Schwann cells (Tsiper M. V. and Yurchenco P. D., 2002). Laminin is a family of heterotrimeric molecules with different combination of alpha, beta, gamma chains. Most common examples of laminin proteins include mouse EHS laminin-1, human placental laminin-2/4, different forms of recombinant laminins and their peptides. EHS Laminin-1 at concentration as low as 2 mkg/ml and placental laminin-2/4 at concentration 20 mkg/ml are able to induce BM assembly on cultured cells in vitro (Tsiper M. V. and Yurchanco P. D., 2002).

Type IV collagen is a non-fibrillar collagen, that is able to assemble into covalently cross-linked network. Type IV collagen is one of the major BM components, which provides structural support and contributes to BM structural stability. Type IV collagen at concentrations of 50-100 mkg/ml is capable of stabilizing differentiated C2C12 myotube BM in vitro (Tsiper M. V., 2002).

Heparan sulfate proteoglycans (HSPG) are a family of membrane or ECM proteins consisting of a protein core and an extended carbohydrate chain. Examples of BM HSPGs are pelican and agrin.

Nidogen is a glycoprotein with binding sites for both laminin and type IV collagen, which is believed to provide a link between the laminin and type IV collagen networks.

According to the major aspect of the invention, other agents can be included in the pharmaceutical compositions, depending on the condition being treated. The pharmaceutical composition may further comprise one or more other compounds, including but not limited to any of the collagens, any laminin types, fibronectin, vitronectin, cadherins, integrins, .alpha.-dystroglycan, nidogen, .alpha.-dystroglycan, glycoproteins, proteoglycans, heparan sulfate proteoglycan, glycosaminoglycans, and peptide fragments thereof. The disclosed compositions may further benefit when used with matrix metalloproteinase inhibitors, which prevent protease-mediated BM degradation as covered by several U.S. patents, for example Patent Application #20020193875 by Amano S., et al. (Dec. 19, 2002).

The following examples are presented to illustrate the process of BM assembly and are not meant to limit the scope of the invention in any way.

Example 1—De novo BM Assembly

This example demonstrates how BM can be assembled de novo on a target cell surface using the disclosed composition. The particular choice of compounds for said composition can be assayed for their ability to mediate BM assembly in a given tissue type, or on a given type of cell surface, using standard assaying techniques. Any suitable assay known to one of skill in the art can be used to monitor such effects. An example of such techniques is described herein.

Cultured primary rat Schwann cells can be used as a test system to evaluate an ability of the compound of interest to initiate/facilitate BM assembly. Same system can be used to determine optimal concentrations. Said assay, referred herein as Schwann cell assay, is described in detail in the publication by the inventor (Tsiper M. V. and Yurchenco P. D., 2002), and has been used further to measure the ability of different compounds to promote BM assembly in another publication by the inventor (Tsiper M. V., 2002).

Briefly, Schwann cells are cultured in the Dulbecco's modified Eagle's medium (DMEM) supplemented with 20% fetal bovine serum and antibiotics (100 units of penicillin and 100 microg of streptomycin/ml), and with growth factors-rich additives, such as Pituitary extract (Sigma, Inc). About 24 hours before applying said composition, the cell medium is replaced with F12 serum-free incubation medium. The assayed component (e.g. genistein) is added to the incubation medium 18 to 0.5 hours before the addition of 2 to 50 microg/ml of laminin-1. After 4 to 18 hours of incubation, the cells are washed, fixed with 3% paraformaldehyde and assayed for the degree of laminin-based BM assembly. The extent of laminin-based BM assembly is evaluated using immunofluorescent microscopy with anti-laminin antibody. BM organization is confirmed using electron microscopy.

Said Schwann cell assay can also be used to determine optimal concentrations of the ingredients of said composition. Other cell lines, such as e.g. Melanoma cell lines, can be used to determine optimal concentrations of the ingredients of said composition related to the cancer type of interest.

Example 2

Stabilization or Strengthening of BM

This example demonstrates how an existing BM can be strengthened (stabilized) on a target cell surface using the disclosed composition. The particular choice of compounds for said composition can be assayed for their ability to strengthen an existing BM in a given tissue type, or on a given type of cell surface, using standard assaying techniques. Any suitable assay known to one of skill in the art can be used to monitor such effects. An example of such techniques is described herein.

Murine C2C12 myoblast cell line can be used as a test system to evaluate an ability of the compound of interest to prevent/disrupt/inhibit/interfere with BM deterioration/disassembly, that is to strengthen a pre-existing BM. Said assay, referred herein as C2C12 BM strengthening assay, is described in detail in the publication by the inventor (Tsiper M. V., 2002). C2C12 cell line is available commercially from American Tissue Culture Collection (ATCC, VA).

Briefly, C2C12 myoblasts are grown in the DMEM supplemented with 20% fetal bovine serum and antibiotics (100 units of penicillin and 100 microg of streptomycin/ml). Myotube formation is induced by switching confluent cells to differentiation media (DMEM supplemented with 2% heat-inactivated horse serum) for 24-72 hours and monitored by morphology. Laminin-based BM forms on the surface of the differentiated C2C12 myotubes within about 4 hours of incubation with 5-10 microg/ml of laminin-1. Said laminin-based BM is highly unstable and disappears from the myotube surface at longer incubations (18 to 24 hours) unless artificially strengthened. The strengthening effectiveness is evaluated by the degree of myotube coverage with laminin, visualized using immunoflourescience microscopy with anti-laminin antibody. BM organization is confirmed using electron microscopy.

Said C2C12 BM strengthening assay can also be used to determine the optimal concentration of the ingredients of said composition. Other cell lines, such as e.g. Melanoma cell lines, can be used to determine optimal concentrations of the ingredients of said composition related to the cancer type of interest.

Example 3

Assessment of Composition Effectiveness with Respect to Manipulating the BM Anti-Invasion Potential This example demonstrates how the effectiveness of various compounds with respect to manipulating the BM anti-invasion potential can be directly assessed/evaluated, using standard assaying techniques. Any suitable assay (for example the one described in Parish C. R., et al., 1992 or Wakabayashi H. and Nicolson G. L., 1998) known to one of skill in the art can be used to monitor such effects An example of such techniques is described herein.

Transwell cell culture chambers (Corning Costar No. 3422. Cambridge. Mass. USA) with a polycarbonate filter of 8.0 mm pore size, separating the upper and lower chambers, can be used as a test system to evaluate an ability of the compound of interest to affect the BM anti-invasion potential. Said assay, referred herein as anti-invasion assay, is described in detail elsewhere.

Briefly, two cell types can be used in said invasion assay, one cell type being assayed for either BM competency or BM strengthening potential whereas the other cell type being monitored for the ability to migrate between said chambers. The following sequence of steps can be used:
1) Cells of type I are seeded onto the upper surface of said filter and allowed to adhere and spread. For example, cultured primary Schwann cells can be used for this purpose.
2) The composition to be evaluated is added and incubated for 4-8 hours. For example, BM assembly on the surface of Schwann cells is achieved by incubation with 2-10 microg/ml of laminin-1 and 50-150 microM genistein for 4-8 hours.
3) BM formation is evaluated either by live immuno-fluorescent microscopy with anti-laminin antibody, or by electron microscopy upon fixation. For example, the degree of BM formation can be evaluated by live immuno-fluorescence of surface-bound laminin with laminin-specific antibody (commercially available from Sigma, Inc.).
4) Cells of type II are added to said upper compartment, i.e. seeded onto the pre-assembled BM and incubated for 8 to 24 hours. For example, HBL, C8161 or A375SM human metastatic melanoma cell lines can be used (commercially available from ATCC, VA, USA).
5) Upon the incubation the cultures are washed and the cells on said upper surface of said filter are removed by wiping with a cotton swab. Said lower surface of said filter is subjected for to visible light microscopic analysis to determine the fraction of cells that have migrated (invaded) said lower filter surface. Immunofluorescent microscopy can be used to determine the cell type specificity using cell type specific markers. Alternately, metabolically labeled or fluorescently-labeled cells can be used for the incubation in order to distinguish between said two cell types.

Preferred Embodiment

Operation, Regime and Dosing for Therapeutic Applications

Actual dosage concentrations of individual ingredients of the disclosed composition administered to a patient can be determined by physical and physiological factors such as body weight, severity of condition, the type of disease being treated, previous or concurrent therapeutic interventions and on the route of administration. The practitioner responsible for administration can determine the concentration of active ingredients of the disclosed composition and appropriate doses for the individual subject. The dosage depends upon the age, sex, health, and weight of the recipient, kind of concurrent therapy, if any, and frequency of treatment and may readily be determined by one skilled in the art.

Preparations of the disclosed composition for administration include sterile aqueous or non-aqueous solutions, suspensions, and emulsions, which may contain pharmaceutical agents which are known in the art. Pharmaceutical compositions such as tablets, pills, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to standard methods. The disclosed composition can be used in a variety of dosage forms, with the preferred form depending upon the mode of administration and the therapeutic application. Optimal dosages and modes of administration for an individual patient can readily be determined by a skilled practitioner.

The regime of administration of the disclosed composition includes oral, intravenous, intra-peritoneal, intra-muscular, subcutaneous, intra-articular, intra-nasal, intra-thecal, intradermal, transdermal or by inhalation. The regime and dose of administration of the disclosed composition that is effective for formation and/or strengthening of BM in the particular subject may readily be determined by one skilled in the art.

The compounds for use in the present invention can be administered as a pharmaceutical composition. The pharmaceutical compositions will generally contain from about 0.0001 to 90 wt. %, preferably about 0.01 to 10 wt. % of the active ingredient by weight of the total composition. In addition to the active agent, the pharmaceutical compositions and medicaments can also contain other pharmaceutically active compounds. The total dose required for each treatment may be administered by multiple doses or in a single dose. Effective amount is referred herein as the most preferable concentration. Other concentrations beyond the range of effective amounts may be used when warranted by clinical objective. Amounts lesser then effective amount can be used if administered locally.

Effective amount of structural BM component, which is a part of the disclosed composition, is 0.01 mkg to 1 g per 1 kg body weight, and preferably from 10 mkg to 50 mg per 1 kg body weight. Effective amount of phytoestrogenic isoflavone in the disclosed composition is 0.02 mkg to 500 mg per 1 kg body weight, and preferably from 5 mkg to 500 mg per 1 kg body weight. Effective amount of actin cytoskeleton perturbing agent is 0.01 mkg to 100 mg. per 1 kg body weight, and preferably from 1 mkg to 50 mg. per kg body weight. Effective amount of phospho-tyrosine kinase inhibitors in the disclosed composition is 0.01 mkg to 100 mg per 1 kg body weight, and preferably from 5 mg. to 50 mg per 1 kg body weight.

The dosage regimen for every component of the disclosed composition may vary widely, but can be determined routinely by a physician using standard methods. Thus, effective doses as low as pico gramm per milliliter are possible if the delivery is optimized.

Another Embodiment

In this embodiment said physical obstacle against tumor invasion comprises a bio-compatible synthetic material, such as a polymer or an artificial implant. Bio-compatible materials represent all materials suitable for implantation into the body. Known bio-compatible materials include polymers, metals, advanced ceramics, composites, coatings, etc. Polymers are compounds that consist of repeating units, or isomers, strung together in chains. Bio-compatible polymers form a large and growing group of materials with a broad spectrum of applications and include biodegradable polymers, bioactive polymers (polypeptides), hydrogels, molecular imprinted polymers, conductive polymers and others. The method for providing a synthetic bio-compatible polymeric barrier, with emphasis to application of a polymeric material to a tissue or cellular surface such as the interior surface of a blood vessel, tissue lumen or other hollow space, is disclosed for example in U.S. Pat. No. 5,843,156 (Slepian M., et al., 1998). The polymeric materials are selected from those materials which can be polymerized or their viscosity altered in vivo by application of exogenous means, for example, by application of light, ultrasound, radiation, or chelation, alone or in the presence of added catalyst. PVC (poly-vinyl chloride) accounts for 80% of polymer consumption as bio-compatible material; other polymers commonly consumed are silicone, polyurethane, polycarbonates, polyester and polyethylene (PE) that are all commercially available. Low-density polyethylene serves as tubing in catheters, ultra-high-molecular-weight (UHMW) polyethylene is one of the major articulating surfaces used in total hip or knee replacements.

Particular examples of bio-compatible polymers are tissue adhesives, or surgical glues. Tissue adhesives (surgical glues) are non-toxic biological substances used by surgeons to join tissues, to suture wounds and blood vessels. A variety of tissue adhesives is available commercially, such as Bioglue (CryoLife, Inc.), ADCON (Gliatech, Inc.), Indermil (Tyco Healthcare), Matrix Collagen Particles (Collagen Matrix, Inc.) etc.

Tissue adhesives can be based on proteins (such as Bioglue®), non-biological materials (such as Indermil®), or composite materials (for example, composition of a natural synthetic peptide(s) including structural and serum proteins and a supporting material including proteoglycan(s), as disclosed in U.S. Pat. No. 5,209,776 (Bass L. S., et al., 1993). Bioglue®, for example, is a protein-based tissue adhesive comprising bovine serum albumin cross-linked with gluteraldehyde, which is widely used in vascular surgery, since it provides an efficient mechanical barrier against liquids.

Another class of protein-based tissue adhesives is represented by fibrin sealants. These materials, composed preliminary of fibrinogen and thrombin, are also commonly used in surgery for tissue sealing, haemostasis, and healing wounds. Said fibrin sealant can be purified from human plasma either autologously, for example, using the procedure disclosed in U.S. Pat. No. 6,613,325 (Amery et al., 2003), or from non-autologous sources. Said fibrin sealants from non-autologous sources are commercially available, for example TISSEEL VH Fibrin Sealant from Baxter Healthcare Corp., CA, U.S. The commercial product is usually a two-component system from human plasma. The first component normally contains highly concentrated fibrinogen, factor VIII, fibronectin, and traces of other plasma proteins. The second component contains thrombin, calcium chloride, and antifibrinolytic agent such as aprotinin. Mixing of the two components promotes clotting and the formation and fibrin cross-linking. The resulting fibrin clot or film adheres to tissues to stop bleeding and improves wound healing (for review see Thompson D. F. et al., 1988).

Indermil (commercially available from Tyco Healthcare) is an example of non-biological tissue adhesive, comprising n-Butyl-2-Cyanoacrylate monomer, which polymerizes upon exposure to water or water-containing substances (tissues). Upon polymerization said Indermil forms a film (solid water-tight seal) that is bound to the underlying surface (Awan K. J. et al, 1974).

Composite tissue adhesives are compositions of peptide(s) and support material, the latter comprising proteoglycans, sacharides, polyalcohols or other components, such as e.g. disclosed in U.S. Pat. No. 5,209,776 (Bass et. al., 1993). Said composite tissue adhesives are capable of forming films (coatings, welds), either spontaneously or upon energy activation. The energy activation usually accelerates the bonding process.

Thus, tissue adhesives exhibit polymeric sealing properties that can be used to reduce the mobility of tissue cells, including cancerous cells, thus reducing the tumor invasion potential. Therefore, introduction of a tissue adhesive into the area of a tumor, or to an immediate proximity of the tumor, for example in a form of a thin film, can create a physical obstacle against tumor invasion, and thus prevent, or significantly delay the tumor invasion stage.

The following example is presented to illustrate the use of a tissue adhesive as a physical obstacle against tumor invasion, and is not meant to limit the scope of the invention in any way.

Example 1

Tissue Adhesive Introduced Via a Surgical Procedure

Introduction of a tissue adhesive in the proximity of a tumor can be routinely performed during a surgical intervention. The tissue adhesive is introduced in the form of a film or a seal, separating the tumor from the healthy tissue in certain most critical directions. Sealing properties of the tissue adhesive will work towards reducing mobility of tissue cells, including the cancerous cells, thus reducing the tumor invasion potential. This procedure can be either a part of a regular cancer surgery, or a surgical intervention can be undertaken for the sole purpose of introducing a physical obstacle in the form of the tissue adhesive.

Said procedure can be performed without surgical removal of the tumor, for example, in the course of biopsy examination. Otherwise, the procedure can also be beneficial when the tumor is surgically removed, in which case introduction of a tissue adhesive will reduce the mobility of the residual left-behind cancerous cells, thus preventing after-surgical recurrence of cancer.

Tissue adhesives such as Indermil, normally come in ampules which release it on application of light pressure. Application procedure of tissue adhesive is routine for a person skilled in art, and is performed in two steps:
1. The target area is cleaned and dried. Excessive blood is debrided and removes when necessary.

2. The tissue adhesive is applied sparingly as a thin film to cover the entire target area.

Example 2

Tissue Adhesive Introduced Via a Non-Surgical Procedure

Since tissue adhesives usually exist in the form of two-component liquids, it is possible to introduce these liquid components to the target area by means of injection through skin.

Third Embodiment

In this embodiment said physical obstacle against tumor invasion comprises a hydrogel. Hydrogels are insoluble polymer structures that form a hydrophilic cross-linked network that swells in water until an equilibrium is reached between the retractive force of the network and the thermodynamic swelling force. Hydrogels exhibit excellent biocompatibility, low degradation and processing ease. Hydrogels can be produced with a wide range of swelling characteristics, which play a major role in determining solute diffusion rates, surface properties, and mechanical characteristics. Cellulose derivatives such as poly(vinyl alcohol) (PVA), poly(ethylene glycol) (PEG), and poly(N-vinyl 2-pyrrolidone) (PNVP), poly(hydroxyethyl methacrylate) (PHEMA) and its derivatives are examples of the most common hydrogel precursors. Hydrogel materials are used extensively in medicine as contact lenses, linings for implants and other applications.

Some types of hydrogels can be photopolymerized in situ using specific light-sensitive compounds, called photoinitiators, and radiation (visible or ultraviolet light). Light exposure of photoinitiators creates free radicals that initiate polymerization of soluble monomeric precursors to form cross-linked hydrogels. Photoinitiated polymers are widely used, for example, in dentistry and also in drug delivery, where several drug delivery systems that utilize photoinitiated polymers have been developed recently. The hydrogels used in drug-delivery systems are normally biodegradable. For the purpose of this invention it is preferable to use slow degradable or nondegradable hydrogels, e.g. such that are used in dentistry. The mechanism of action here is basically the same as in a drug delivery system, with the distinction that the hydrogel itself, and not an anticancer medicine, is the object of targeted delivery to the area of the tumor.

Photopolymerazation conditions are normally mild and physiologically compatible (highly controllable initiation of polymerization, physiological conditions of polymerization (temperature and pH), low light intensity, short irradiation times), therefore photopolymerization can be carried out in direct contact with living cells and tissues. The attainability of in situ hydrogel photopolymerization allows for local targeted application minimizing damage to healthy tissues. In situ formation of photopolymerized hydrogels is accomplished either in bulk or using interfacial photopolymerization. In case of bulk photopolymerization monomers and photoinitiators are both present in the solution and polymerization occurs upon exposure to the appropriate wavelength of light. In interfacial polymerization photoinitiator is adsorbed onto the surface of interest and polymerization occurs upon exposure to hydrogel precursor and the appropriate wavelength of light at the tissue interface, i.e. where the hydrogel precursor comes into contact with the photoinitiator. Interfacial polymerization allows for the creation of hydrogel linings on live cells and tissues. The degradation rate and permeability of the hydrogel can be altered by changing the composition of the precursors, allowing use of this class of materials for a variety of tumor types and stages of progression.

The following example is presented to illustrate the use of a hydrogel as a physical obstacle against tumor invasion, and is not meant to limit the scope of the invention in any way.

Example

Formation of Blood Vessel Invasion Obstacle Using In Situ Photoinduced Polymerization In situ photo-induced polymerized hydrogels can be used to perform internal arterial lining in order to prevent or delay vessel wall penetration by tumor cells. Specifically, photo-induced polymerization of polyethleneglycol diacrylate (PEG-DA) is used to form hydrogel layers lining (coating) the intima of blood vessels. The possibility to use in situ photo-induced polymerization for in vivo coating of blood vessels by has been demonstrated by Hubbell et al. (An Y. and Hubbell J. A., 2000) and described in U.S. Pat Application 20030087985 (Hubbell et al., 2003).

Water-soluble non-toxic hydrogel precursor polyethileneglycol diacrylate (PEG-DA) which consists of polyethyleneglycol copolymerized with an alpha-hydroxy acid and with acrylate termini at each end, is synthesized as described elsewhere (Cruise G. M., et al, 2000; An Y. and Hubbell J. A., 2000). Alternatively, PEG-DA is commercially available and may be purchased for example from Sartomer (Exton, Pa.). Interfacial polymerization is more favorable for surface coating in order to avoid clamps formation. For interfacial polymerization a photoinitiator, for example 10 nM eosin Y, is applied intraarterially and allowed for adsorption onto vessels intima. Following this, a hydrogel precursor, for example PEG-DA in saline with 0.1 mM triethanolamine and 0.15% N-vinyl pyrrolidinone) is then subjected for inter-arterial perfusion. The area of the body where the obstacle formation is desired is illuminated with an argon ion laser (514 nm) at an intensity of approximately 1 mW/cm$^2$ for 5 seconds using cannula. Alternatively, visible or UV light can be applied transdermally. While light is poorly transmitted through skin, sufficient light does penetrate to convert precursor into the hydrogel on the vessels intima where photoinitiator is adsorbed. Other hydrogel precursors described in U.S. Pat. No. 6,465,001 (Hubbell et al, 2002) can be used as blood vessels obstacle coating, such as PEG-diacrylate derivatives.

Another Embodiment

Growth factors and other agents that stimulate tissue growth are generally contraindicated to cancer patients. However, this embodiment demonstrates use of growth factors in a specific manner to stimulate the patient organism to assemble (grow) a physical obstacle against tumor invasion. Growth factors are small, secreted molecules that stimulate cell signaling through the specific membrane receptors.

Specific growth factors are administered to stimulate growth of a specific tissue (other then cancerous tissue), such as connective tissue, or cartilage, or other tissue which plays a role of said physical obstacle against tumor invasion.

Alternatively, specific growth factors are administered to stimulate expression of specific proteins, such as collagens, laminins, etc., which can participate as assembly blocks in the formation of said physical obstacle against tumor invasion.

For example, application of agents that promote matrix protein production, such as fibroblasts growth factors (FGF), transforming growth factor alpha (TGFα), transforming growth factor beta (TGFβ), epithelium growth factor (EGF), soy bean lysolecithin, promote formation or strengthening of said physical obstacle, including BM as disclosed in U.S. Patent Application 20020193875 (Amano S., et al., 2002).

Another example is enzymatic stimulation of chondrocytes to enhance cartilage production. Cartilage is a form of connective tissue composed of polymorphic cells suspended in highly hydrated, metachromatic colloidal gel matrices of varying rigidity and composition. Chemically, cartilage is characterized by its high content of collagen, glycosaminoglycan complexes, and water. Cartilage can be surgically transplanted or its production and organization into fine structure by chondricytes can be induced (stimulated) by various means, for example, by enzymatic activity, such as a proteoglycanase or a protease, disclosed in U.S. Pat. No. 5,916,557 (Berlowitz-Tarrant L., et al., 1999). Alternatively, artificial cartilage, such as disclosed in U.S. Pat. No. 5,944,755 (Stone K., 1999), may be used as a physical obstacle.

An alternative to cartilage tissue is the use of bone tissue as said physical obstacle. Bone precursor cells, which are not hematopietic, can differentiate into osteoblasts and deposit calcium into the ECM upon exposure to a bone growth factor, as disclosed in U.S. Pat. No. 5,972,703 (Long M. W., 1999). Bone precursor cells differentiation into osteoblasts can be performed either in vivo by administration of bone growth factor(s), or in vitro by isolating bone precursor cells from bone marrow, culturing in the presence of bone growth factor(s), and consecutive transplantation to the desired location. Alternatively, artificial bone material, such as disclosed in U.S. Pat. No. 6,692,760 (Miyamoto T. and Kokubo T., 2004), may be used as a physical obstacle.

RAMIFICATION AND SCOPE

The disclosed method may further benefit if delivered specifically to the area of the tumor or its vicinity using homing techniques or compositions, such as homing molecules disclosed in the U.S. Pat. No. 6,576,239 (Ruoslahti et al., 2003), long polypeptide carrier with attached active agents disclosed in the U.S. Pat. No. 5,762,909 (Uzgiris, et al., 1998), ion exchange tumor targeting using dextran disclosed in U.S. Pat. No. 6,569,841 (Holmberg, et al., 2003) or various apparatus for local delivery of drugs such as the one disclosed in U.S. Pat. No. 5,282,785 (Shapland, et al., 1994), all patents referred herein as examples.

REFERENCES CITED

U.S. Patent Documents

U.S. Pat. No. 5,055,298 Kludas: Cosmetic composition comprising an extracellular connective tissue matrix. 1991
U.S. Pat. No. 5,209,776 Bass et. al.: Tissue bonding and sealing composition and method of using the same. 1993
U.S. Pat. No. 5,211,657 Yamada, et al.: Laminin a chain deduced amino acid sequence, expression vectors and active synthetic peptides. 1993
U.S. Pat. No. 5,282,785 Shapland J. E., et al.: Drug delivery apparatus and method. 1994
U.S. Pat. No. 5,762,909 Uzgiris E. E.: Tumor targeting with polymeric molecules having extended conformation. 1998
U.S. Pat. No. 5,843,156 Slepian M., et al.: Local polymeric gel cellular therapy. 1998
U.S. Pat. No. 5,911,995 Uckun: EGF-genistein conjugates for the treatment of cancer. 1999
U.S. Pat. No. 5,916,557 Berlowitz-Tarrant, et al.: Methods of repairing connective tissues. 1999
U.S. Pat. No. 5,944,755 Stone K.: Articular cartilage xenografts. 1999
U.S. Pat. No. 5,972,703 Long, et al.: Bone precursor cells: compositions and methods. 1999
U.S. Pat. No. 6,153,593 Burgeson, et al.: Laminin 5 and the formation of basement membrane structure. 2000
U.S. Pat. No. 6,395,279 Empie, et al.: Method of preparing and using isoflavones for the treatment of cancer. 2002
U.S. Pat. No. 6,465,001 Hubbell, et al.: Treating medical conditions by polymerizing macromers to form polymeric materials. 2002
U.S. Pat. No. 6,497,906 Kelly G. E.: Dietary supplements comprising soy hypocotyls containing at least one isoflavone. 2002
U.S. Pat. No. 6,569,841 Holmberg A.: Ion exchange tumor targeting (IETT). 2003
U.S. Pat. No. 6,576,239 Ruoslahti E.: Angiogenic homing molecules and conjugates derived therefrom. 2003
U.S. Pat. No. 6,613,325 Amery et al.: Prevention of post surgical adhesions using a fibrin monomer sealant. 2003
U.S. Pat. No. 6,692,760 Miyamoto T., et al.: Polymeric material for artificial bone. 2004
20020193875 Amano S., et al.: Agent promoting the formation of skin basement membrane, agents promoting the formation of artificial skin and process for producing artificial skin. 2002
20030087985 Hubbell et al.: Gels for encapsulation of biological materials. 2003

Other References

1. Akashi T., Ito E., Eishi Y., Koike M., Nakamura K., Burgeson R. E.: Reduced expression of laminin alpha 3 and alpha 5 chains in non-small cell lung cancers. Jpn J Cancer Res., 92(3):293-301, 2001
2. Akashi T., Miyagi T., Ando N., Suzuki Y., Nemoto T., Eishi Y., Nakamura K., Shirasawa T., Osa N., Tanaka N., Burgeson R. E.: Synthesis of basement membrane by gastrointestinal cancer cell lines. J. Pathol., 187(2):223-8, 1999
3. Alberts B., Bray D., Lewis J., Raff M., Roberts K., Waatson J. D.: Molecular Biology of The Cell. Third Ed. Garland Publishing, Inc., Chapter 19: Cell Junctions, Cell Adhesion, and the Extracellular Matrix. 1994
4. Alfaro-Lopez J., Yuan W., Phan B. C., Kamath J., Lou Q., Lam K. S., Hruby V. J.: Discovery of a novel series of potent and selective substrate-based inhibitors of p60c-src protein tyrosine kinase: conformational and topographical constraints in peptide design. J Med Chem. 41(13): 2252-60, 1998
5. Al-Obeidi F. A. and Lam K. S.: Development of inhibitors for protein tyrosine kinases. Oncogene. 19(49):5690-701, 2000
6. An Y., Hubbell J. A.: Intraarterial protein delivery via intimally-adherent bilayer hydrogels. J. of Controlled Release, 64: 205-215, 2000
7. Awan K. J., Spaeth P. G.: Use of Isobutyl-2-Cyanoacrylate Tissue Adhesive in the Repair of Conjunctional Fistula in Filtering Procedures for Glaucoma. Ann Ophthalmol. 6(8): 851-3, 1974
8. Baselga J.: Clinical trials of Herceptin (trastuzumab). Eur J. Cancer. 37 Suppl. 1: S 18-24, 2001
9. Birkedal-Hansen H.: Proteolytic remodeling of extracellular matrix. Curr Opin Cell Biol 7: 728-735, 1995

10. Birt D. F., Hendrich S., Wang W.: Dietary agents in cancer prevention: flavonoids and isoflavonoids. Pharmacol Ther. 90(2-3): 157-77, 2001
11. Braunwalder A. F., Yarwood D. R., Sills M. A., Lipson K. E.: Measurement of the protein tyrosine kinase activity of c-src using time-resolved fluorometry of europium chelates. Anal Biochem. 238(2): 159-64, 1996
12. Colognato H., Winkelmann D. A., Yurchenco P. D.: Laminin polymerization induces a receptor-cytoskeleton network. J Cell Biol. 145(3): 619-31, 1999
13. Colorado P. C., Torre A., Kamphaus G., Maeshima Y., Hopfer H., Takahashi K., Volk R., Zamborsky E. D., Herman S., Sarkar P. K., Ericksen M. B., Dhanabal M., Simons M., Post M., Kufe D. W., Weichselbaum R. R., Sukhatme V. P., Kalluri R.: Anti-angiogenic cues from vascular basement membrane collagen. Cancer Res., 60(9):2520-6, 2000.
14. Coussens L. M., Fingleton B. and Matrisian L. M.: Matrix metalloproteinase inhibitors and cancer: trials and tribulations. Science 295, 2387-2392, 2002
15. Cruise G. M., Hegre O. D., Scharp D. S., Hubbell J. A.: A sensitivity study of the key parameters in the interfacial photopolymerization of poly(ethylene glycol) diacrylate upon porcine islet. Biotechnology and Bioengineering, 57(6): 655-665, 2000
16. Drummond A. H., Beckett P., Brown P. D., Bone E. A., Davidson A. H., Galloway W. A., Gearing A. J., Huxley P., Laber D., McCourt M., Whittaker M., Wood L. M., Wright A.: Preclinical and clinical studies of MMP inhibitors in cancer. Ann N Y Acad Sci 878, 228-235, 1999
17. Fidler I. J.: Molecular biology of cancer: invasion and metastasis. In: V. T. Devita Jr., S. Hellman and S. A. Rosenberg (eds.) Cancer: Principles and Practice of Oncology, 5th ed. Lippincott-Raven Publishers, Philadelphia, pp. 135-152, 1997
18. Gingras D., Boivin D., Deckers C., Gendron S., Barthomeuf C., Beliveau R.: Neovastat-a novel antiangiogenic drug for cancer therapy. Anticancer Drugs 14, 91-96, 2003
19. Glass D. B., Trewhella J., Mitchell R. D., Walsh D. A.: Conformationally constrained analogs of protein kinase inhibitor (6-22)amide: effect of turn structures in the center of the peptide on inhibition of cAMP-dependent protein kinase. Protein Sci. 4(3): 405-15, 1995
20. Ikenaka Y., Yoshiji H., Kuriyama S., Yoshii J., Noguchi R., Tsujinoue H., Yanase K., Namisaki T., Imazu H., Masaki T., Fukui H.: Tissue inhibitor of metalloproteinases-1 (TIMP-1) inhibits tumor growth and angiogenesis in the TIMP-1 transgenic mouse model. Int J Cancer 105, 340-346, 2003
21. Jouan V., Canron X., Alemany M., Caen J. P., Quentin G., Plouet J., Bikfalvi A.: Inhibition of in vitro angiogenesis by platelet factor-4-derived peptides and mechanism of action. Blood 94: 984-993, 1999
22. Kamphaus G D, Colorado P C, Panka D J, Hopfer H, Ramchandran R, Torre A, Maeshima Y, Mier J W, Sukhatme V P, Kalluri R.: Canstatin, a novel matrix-derived inhibitor of angiogenesis and tumor growth. J Biol Chem. 14; 275(2): 1209-15, 2000
23. Lafleur M. A., Handsley M. M. and Edwards D. R.: Metalloproteinases and their inhibitors in angiogenesis. Exp. Rev. Mol. Med. Vol. 5, 2003
24. Lee M. M., Gomez S. L., Chang J. S., Wey M., Wang R. T., Hsing A. W.: Soy and isoflavone consumption in relation to prostate cancer risk in China. Cancer Epidemiol Biomarkers Prey. 12(7): 665-8, 2003
25. Levitt M. L. and Koty P. P.: Tyrosine kinase inhibitors in preclinical development. Invest New Drugs. 17(3): 213-26, 1999
26. Li H., Lindenmeyer F., Grenet C., Opolon P., Menashi S., Soria C., Yeh P., Perricaudet M., Lu H.: AdTIMP-2 inhibits tumor growth, angiogenesis, and metastasis, and prolongs survival in mice. Hum Gene Ther. 12(5): 515-26, 2001
27. Liotta L. A., Kohn E. C.: The microenvironment of the tumor-host interface. Nature 411, 375-379, 2001
28. Liotta L. A., Steeg P. S., Stetler-Stevenson W. G.: Cancer metastasis and angiogenesis: an imbalance of positive and negative regulation. Cell, 64: 327-336, 1991
29. Maeshima Y., Sudhakar A., Lively J. C., Ueki K., Kharbanda S., Kahn C. R., Sonenberg N., Hynes R. O., Kalluri R.: Tumstatin, an endothelial cell-specific inhibitor of protein synthesis. Science, 295(5552):140-3, 2002
30. Maeshima Y., Mier J. W., Sukhatme V. P., Kalluri R.: Canstatin a novel matrix-derived inhibitor of angiogenesis and tumor growth. J Biol Chem 275, 1209-1215, 2000
31. Mendel D. B., Schreck R. E., West D. C., Li G., Strawn L. M., Tanciongco S. S., Vasile S., Shawver L. K., Cherrington J. M.: The angiogenesis inhibitor SU5416 has long-lasting effects on vascular endothelial growth factor receptor phosphorylation and function. Clin Cancer Res 6, 4848-4858, 2000
32. Monti E., Sinha B. K.: Antiproliferative effect of genistein and adriamycin against estrogen-dependent and -independent human breast carcinoma cell lines. AntiCancer Res. 14(3A):1221-1226, 1994
33. Ogawara H., Akiyama T., Ishida J., Watanabe S., Suzuki K.: A specific inhibitor for tyrosine protein kinase from Pseudomonas. J Antibiot (Tokyo). 39(4): 606-8, 1986
34. Parish C. R., Jakobsen K. B., Coombe D. R.: A basement-membrane permeability assay which correlates with the metastatic potential of tumour cells. Int J. Cancer. 52(3): 378-83, 1992
35. Ponce M. L., Hibino S., Lebioda A. M., Mochizuki M., Nomizu M., Kleinman H. K.: Identification of a potent peptide antagonist to an active laminin-1 sequence that blocks angiogenesis and tumor growth. Cancer Res. 63(16): 5060-4, 2003
36. Sandberg J. A., Bouhana K. S., Gallegos A. M., Agrawal A. B., Grimm S. L., Wincott F. E., Reynolds M. A., Pavco P. A., Parry T. J.: Pharmacokinetics of an antiangiogenic ribozyme (ANGIOZYME) in the mouse. Antisense Nucleic Acid Drug Dev 9, 271-277, 1999
37. Seethala R., Menzel R.: A fluorescence polarization competition immunoassay for tyrosine kinases. Anal Biochem. 255(2): 257-62, 1998
38. Shalinsky D. R., Brekken J., Zou H., McDermott C. D., Forsyth P., Edwards D., Margosiak S., Bender S., Truitt G., Wood A., Varki N. M., Appelt K.: Broad antitumor and antiangiogenic activities of AG3340, a potent and selective MMP inhibitor undergoing advanced oncology clinical trials. Ann N Y Acad Sci 878, 236-270, 1999
39. Stebbing J., Copson E., O'Reilly S.: Herceptin (trastuzumab) in advanced breast cancer. Cancer Treat Rev. 26(4): 287-90, 2000
40. Stetler-Stevenson W. G., Aznavoorian S., Liotta L. A.: Tumor cell interactions with the extracellular matrix during invasion and metastasis. Ann. Rev. Cell Biol., 9: 541-573, 1993
41. Thompson D. F., Letassy N. A., Thompson G. D.: Fibrin Glue: a review of its preparation, efficacy and adverse effects as a topical hemostat", Drug Intell. Clin. Pharm. 22: 946-952, 1988

42. Tsiper M. V.: Basement membrane assembly on Schwann cell and myotube surfaces. Ph.D. Theses, 2002
43. Tsiper M. V. and Yurchenco P. D.: Laminin assembles into separate basement membrane and fibrillar matrices in Schwann cells. J Cell Sci. 115(Pt 5):1005-15, 2002
44. Wakabayashi H. and Nicolson G. L.: Transfilter cell invasion assays. In: J. E. Celis (ed.) Cell Biology: A Laboratory Handbook, 2nd ed. Academic Press, San Diego, pp. 296-301, 1998
45. Wilson D. F., Jiang D. J., Pierce A. M., Wiebkin O. W.: Oral cancer: role of the basement membrane in invasion. Aust Dent J.: 44(2):93-7, 1999
46. Wojtowicz-Praga S. M., Dickson R. B., Hawkins M. J.: Matrix metalloproteinase inhibitors. Invest New Drugs. 15(1): 61-75, 1997
47. Wu A. H., Yu M. C., Tseng C. C., Twaddle N. C., Doerge D. R.: Plasma isoflavone levels versus self-reported soy isoflavone levels in Asian-American women in Los Angeles County. Carcinogenesis 25(1): 77-81, 2004
48. Wu A. H., Wan P., Hankin J., Tseng C. C., Yu M. C., Pike M. C.: Adolescent and adult soy intake and risk of breast cancer in Asian-Americans. Carcinogenesis 23, 1491-1496, 2002
49. Yancopoulos G. D., Davis S, Gale N W, Rudge J S, Wiegand S J, Holash J.: Vascular-specific growth factors and blood vessel formation. Nature 407, 242-248, 2000

What claimed is:

1. A composition for impeding cancerous cells invasion, said composition comprising:
   a) means for enabling cell basement membrane competency, and
   b) one or more structural basement membrane protein wherein the amount of said means for enabling cell basement membrane competency and the amount of said structural basement membrane protein(s) are effective in synergistically promoting basement membrane assembly, strengthening or de-novo formation by tissue cells wherein said synergistic promotion from the amount of said means and said structural basement membrane protein is greater than the theoretical additive effect of combined said means and said structural basement membrane protein.

2. The composition of claim 1 comprising a pharmaceutically available carrier.

3. The composition of claim 1 wherein said means comprise phytoestrogenic isoflavone.

4. The composition of claim 1 wherein said means comprise soy isoflavone.

5. The composition of claim 1 wherein said means comprise genistein.

6. A composition comprising a) one or more structural basement membrane proteins selected from the group consisting of laminin, type IV collagen, nidogen, heparan sulfate proteoglycan, and b) one or more substance selected from the group consisting of phytoestrogenic isoflavone, genistein, actin cytoskeleton reorganization inhibitor, Cytochalasin D, phospho-tyrosine kinase inhibitor,
   wherein the amount of said structural basement membrane protein(s) and the amount of said substance(s) are effective in synergistically promoting basement membrane assembly, strengthening or de-novo formation, and wherein said synergistic promotion from the amount of said substance and said structural basement membrane protein is greater than the theoretical additive effect of combined said substance and said structural basement membrane protein.

7. The composition of claim 6 wherein said structural basement membrane protein is laminin and said substance is genistein.

* * * * *